(12) United States Patent
Smith et al.

(10) Patent No.: US 11,337,846 B2
(45) Date of Patent: May 24, 2022

(54) ELONGATED SLEEVE FOR BRACING A HUMAN PENIS DURING ERECTILE DISFUNCTION

(71) Applicants: Nanci Smith, Haughton, LA (US); Brian Smith, Haughton, LA (US)

(72) Inventors: Nanci Smith, Haughton, LA (US); Brian Smith, Haughton, LA (US)

(*) Notice: Subject to any disclaimer, the term of this patent is extended or adjusted under 35 U.S.C. 154(b) by 0 days.

(21) Appl. No.: 16/375,815

(22) Filed: Apr. 4, 2019

(65) Prior Publication Data

US 2020/0360172 A1 Nov. 19, 2020

(51) Int. Cl.
*A61F 5/41* (2006.01)

(52) U.S. Cl.
CPC .......... *A61F 5/41* (2013.01); *A61F 2005/411* (2013.01)

(58) Field of Classification Search
CPC ..... A61F 5/41; A61F 2005/411; A61H 19/50; A61H 19/00; A61H 19/30; A61H 19/32
USPC ...................................... 600/38–41
See application file for complete search history.

(56) References Cited

U.S. PATENT DOCUMENTS

| | | | | |
|---|---|---|---|---|
| 4,224,933 A * | 9/1980 | Reiling | ..................... | A61F 5/41 600/39 |
| 5,622,186 A * | 4/1997 | Schwartz | ................. | A61F 5/41 128/842 |
| 6,793,620 B1 * | 9/2004 | Droznin | ..................... | A61F 5/41 600/39 |
| 2009/0069629 A1 * | 3/2009 | Uson Calvo | ........... | A61H 19/34 600/38 |
| 2013/0253264 A1 * | 9/2013 | Canbulat | ................ | A61H 19/32 600/38 |
| 2013/0296645 A1 * | 11/2013 | Evans | ..................... | A61H 19/40 600/41 |
| 2014/0073851 A1 * | 3/2014 | Gioia | ........................ | A61H 1/02 600/38 |
| 2017/0172784 A1 * | 6/2017 | Kiefer | ........................ | A61F 5/41 |
| 2019/0060103 A1 * | 2/2019 | Fielding | .................... | A61F 5/41 |

OTHER PUBLICATIONS

Nylon definition from Wikipedia. Printed May 8, 2021. (Year: 2021).*

* cited by examiner

*Primary Examiner* — Samuel G Gilbert
(74) *Attorney, Agent, or Firm* — Patrick Mixon

(57) ABSTRACT

An elongated sleeve for use by men suffering erectile disfunction is described that includes a first open end for leaving the penis head and base of the penis body exposed to tactile stimulation. The invention teaches penile support braces which prop up a semi-erect penis during intercourse.

16 Claims, 7 Drawing Sheets

ELONGATED SLEEVE FOR BRACING A HUMAN PENIS DURING ERECTILE DISFUNCTION

RELATED APPLICATIONS 1791

Field of Invention

The present invention relates to a sexual aid, and more particularly, the invention relates to a support for

BACKGROUND OF THE INVENTION

A gratifying sexual experience for both adult participants often depends on the male's penis maintaining an erection throughout the encounter. The experience becomes less gratifying for participants when the male's penis becomes semi-erect or flaccid during copulation. When a male repeatedly experiences a semi-erect or flaccid penis during sex, the male is likely experiencing erectile disfunction (ED), which often ruins the denouement of the experience. Consequently, men have been looking for a solution for maintaining an erection throughout.

Many men have resulted to a pharmaceutical solution for ED. For example, drugs such as Sildenafil, Tadalafil, Vardenafil, and Avanafil are commonly sold ad medication prescribed to combat ED. Until recently, men could only obtain these medications by prescription. More importantly, these medications are time release, which is not useful for a spontaneous encounter. Further still, these medications are not effective for every male.

Males suffering ED may opt for a penile injection. For example, alprostadil is an ED drug that can be injected directly into the penis to trigger an automatic erection. However, a penile injection is not suitable for males with an aversion to needles. Additionally, users of penile injections have experienced a burning sensation and priapism, an erection that lasts more than four hours and requiring medical treatment.

Males who are unwilling to self-inject alprostadil, may use a medical urethral system (MUSE). MUSE is a dissolvable pellet that can be inserted directly into the urethra, the opening of the opening of the penis. MUSE will trigger an erection in about 10 minutes, and the erection may last one hour. Unfortunately, Muse users have reported somewhat unpleasant side effects, such as, an aching burning sensation, and redness and minor bleeding.

In some instances, males experiencing ED may use a vacuum pump, where a plastic cylinder is placed over the penis. A pump removes the air out of the cylinder to force blood flow into the penis. An elastic ring is placed at the base (e.g., root) of the penis to hold the erection. In this way, the state of erectness of the penis is mechanically altered. Unfortunately, the vacuum pump may cause numbness, bruising, and weak ejaculation.

A penile implant is another solution for maintaining an erect penis during sexual intercourse. Penile implants are devices placed inside the penis to allow me with ED to get and maintain an erection. Penile implants can be either semirigid or inflatable. However, although penile implants have proven to be effective, penile implants are invasive to the human body in that they require surgery to insert the implant into the penis. Such surgeries may lead to an infection, such as, pulmonary infection, or urinary tract infection. These issues are especially problematic for diabetic men, where an infection can lead to amputation.

As can be seen, prior art solutions for ED use pharmaceuticals that may fail, are invasive, or come with unpleasant side effects. Therefore, what is needed is an apparatus that will help a semi-erect penis simulate that the penis is in an erect state during intercourse that is not invasive, and does not have the adverse affects found in the prior art. Such an apparatus may provide brace the semi-erect human penis, such that brace can assist the human penis to simulate erectness.

SUMMARY OF THE INVENTION

The present invention teaches improvments not found in the prior art. In view of the foregoing disadvantages inherent in the methods for treating ED known in the prior art, the present invention provides a nonmedicinal, noninvasive, nonsurgical apparatus which braces a penis experiencing ED to simulate a full erection.

In one aspect, the invention teaches an elongated sleeve for receiving a human penis therein. In another aspect, the elongated sleeve leaved uncovered areas of the human penis important for sexual arousal and stimulation. In yet another aspect, the invention is configured to encourage full erection of the penis, by providing areas for pressure to be applied to the penis during intercourse. In still another aspect, the invention includes penis support braces include in the invention along either side of the penis for supporting the penis in an erect position.

In yet another embodiment, the invention teaches an apparatus for supporting a human penis comprising:
  a. an elongated sleeve for enclosing the shaft of the penis, the elongated sleeve having
    i. a first open end, wherein the first open end is positioned to be in proximity to the neck of the penis when the elongated sleeve is worn,
    ii. a second open end, wherein the second open end is positioned along the length of the elongated sleeve, and wherein the second open end is positioned opposite the first open end, and wherein the second open end is positioned in proximity to the root of the penis when the elongated sleeve is worn,
    iii. a third open end, the third open end being positioned adjacent to the second open end, wherein the third open end is positioned to receive the penis scrotum when the elongated sleeve is worn, and
    iv. at least one elongated penile support brace positioned along a lateral side of the elongated sleeve.

Still another embodiment, the invention teaches an apparatus for supporting a human penis comprising:
  a. an elongated sleeve for enclosing the shaft of the penis, the elongated sleeve having
    v. a first open end, wherein the first open end is positioned to be in proximity to the glans of the penis when the elongated sleeve is worn,
    vi. a second open end, wherein the second open end is positioned along the length of the elongated sleeve, and wherein the second open end is positioned opposite the first open end, and wherein the second open end is positioned to receive the root of the penis when the elongated sleeve is worn,
    vii. a third open end, the third open end being positioned adjacent to the second open end, wherein the third open end is positioned to receive the penis scrotum when the elongated sleeve is worn, and
    viii. wherein the elongated sleeve includes an aperture in proximity to the second open end, wherein the elongated sleeve aperture in proximity to the third open end, and wherein the elongated sleeve aperture is positioned to expose a portion of the base of the penis shaft when the elongated sleeve is worn.

Additionally, the present invention teaches an apparatus for supporting a human penis comprising:
 a. an elongated sleeve for enclosing the shaft of the penis, the elongated sleeve having
  ix. a first open end, wherein the first open end is positioned to be in proximity to the neck of the penis when the elongated sleeve is worn,
  x. a second open end, wherein the second open end is positioned along the length of the elongated sleeve, and wherein the second open end is positioned opposite the first open end, and wherein the second open end is positioned in proximity to the root of the penis when the elongated sleeve is worn,
  xi. a third open end, the third open end being positioned adjacent to the second open end, wherein the third open end is positioned to receive the penis scrotum when the elongated sleeve is worn, and
  xii. at least one elongated penile support brace positioned along a lateral side of the elongated sleeve.

BRIEF DESCRIPTION OF THE DRAWINGS

A more complete understanding of the present invention may be derived by referring to the various embodiments of the invention described in the detailed descriptions and drawings and figures in which like numerals denote like elements, and in which.

DETAILED DESCRIPTION OF PREFERRED EMBODIMENTS

The present invention relates to an apparatus and method for bracing a human penis to enable the penis to simulate full erection. The invention is useful for men who experience ED. In use, a man inserts his penis into the apparatus and the apparatus props the penis up during intercourse.

Figure 1:
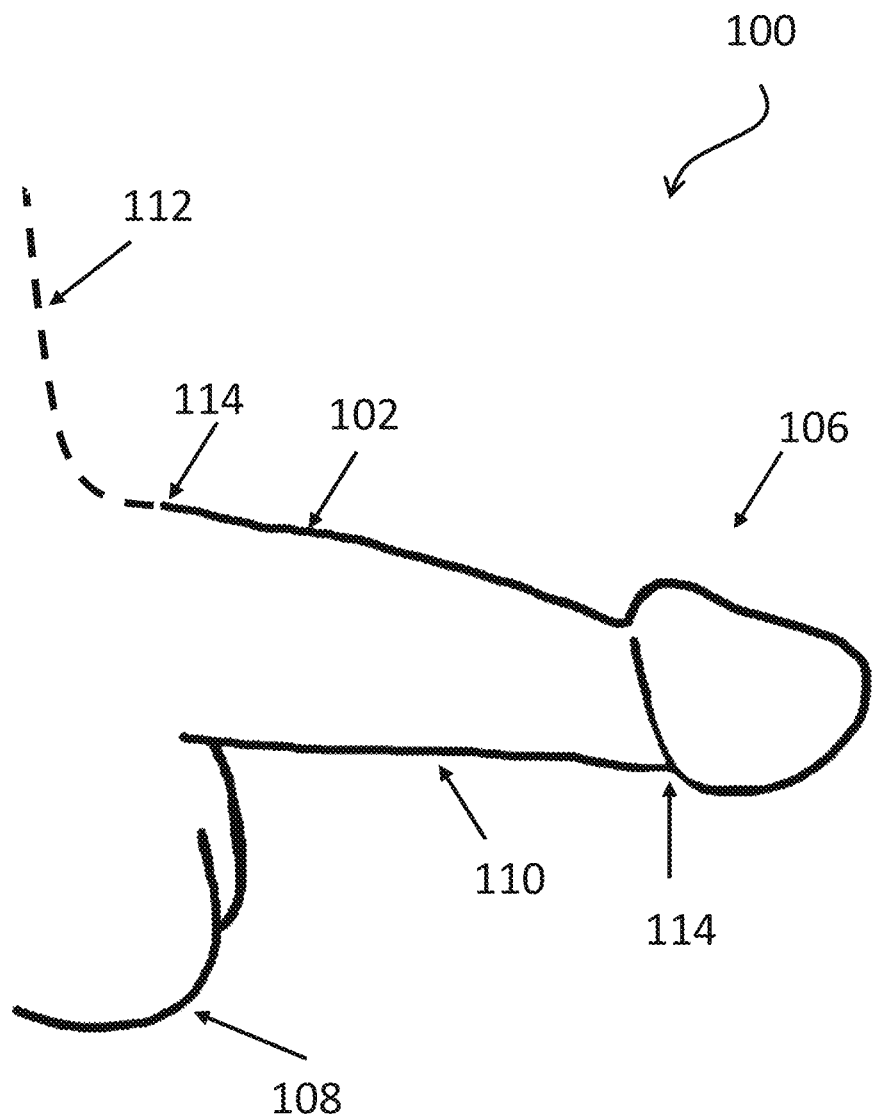
FIG. 1 is an illustration of the human penis, which is the environment in which the present invention may be used.

FIG. 1 is a depiction of a conventional human penis, the environment in which the device is ordinarily used. As shown, human penis 100 comprises a penis body 102. Penis body 102 includes a penis head 106 at a first end. Penis head 106 may be in communication with penis body 102 via a penis neck 114. Penis body 102 includes a penis root 104 on a second end, where penis body 102 is connected to the human body 112. Penis 100 further includes a scrotum 108 in communication with body 102, wherein majority of the mass of the penis scrotum 108 is located below penis body 102. As is generally known, the majority of the mass of a penis scrotum ordinarily comprises testicles that are positioned below the penis body. Accordingly, as described herein, penis scrotum 108 may include testicles which cause the majority of the mass of penis scrotum 108 to be positioned below penis body 102.

It is also well known that the human penis has erogenous zones that enhance a sexual experience when tactilely stimulated. For example, portions of the human head 106 provide sexual stimulation when manipulated. Similarly, penis body 102 may also include an erogenous zone positioned at penis base 110. As used herein, penis base 110 is locate substantially near the bottom penis body 102. More particularly, penis base 110 is locates on penis body 102 and adjacent to penis scrotum 108.

Figure 2:
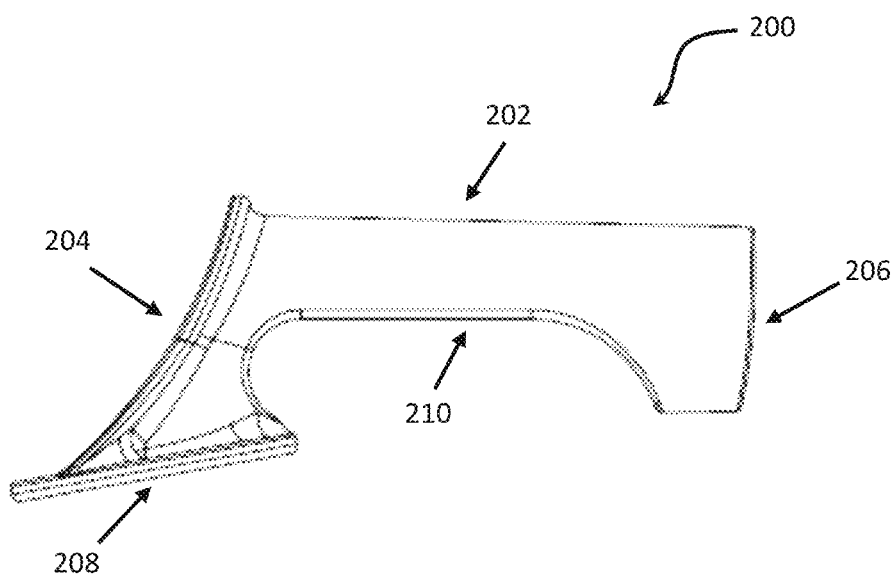
FIG. 2 is a side view of an elongated sleeve in accordance with exemplary embodiments of the present invention.

FIG. 2 is an exemplary side view of an elongated sleeve 200 according to the present invention. As shown, elongated sleeve 200 comprises an elongated sleeve body 202. Elongated sleeve body 202 includes a first open end 206 at a first sleeve end. Elongated sleeve 200 further includes a second open end 204 at a second sleeve end. Elongated sleeve second open end 204 may be located on elongated sleeve 102 in an end of elongated sleeve body 102 opposite first open end 206.

As noted, human penis 100 has erogenous zones that increase sexual pleasure when touched. The present invention's design takes these erogenous zones into account. For example, in use, a human penis 100 is inserted into elongated sleeve 200 such that the penis head 106 is inserted through second open end 204 through first open end 206. In such way, penis head 206 protrudes through first open end 206 and first open end 206 is positioned in proximity to penis neck 114. Additionally, since penis 100 has an erogenous zone at penis base 110, then elongated sleeve body 202 includes an elongated sleeve aperture 210 positioned in proximity to penis base 110.

Elongated sleeve 200 may further include a third opening 208 adjacent to second open end 204. Third opening 208 may be adjacent to elongated sleeve aperture 210. During use of elongated sleeve 200, a user who has inserted his penis 100 into elongated sleeve 200 may further insert his scrotum into third opening 208.

Figure 3:
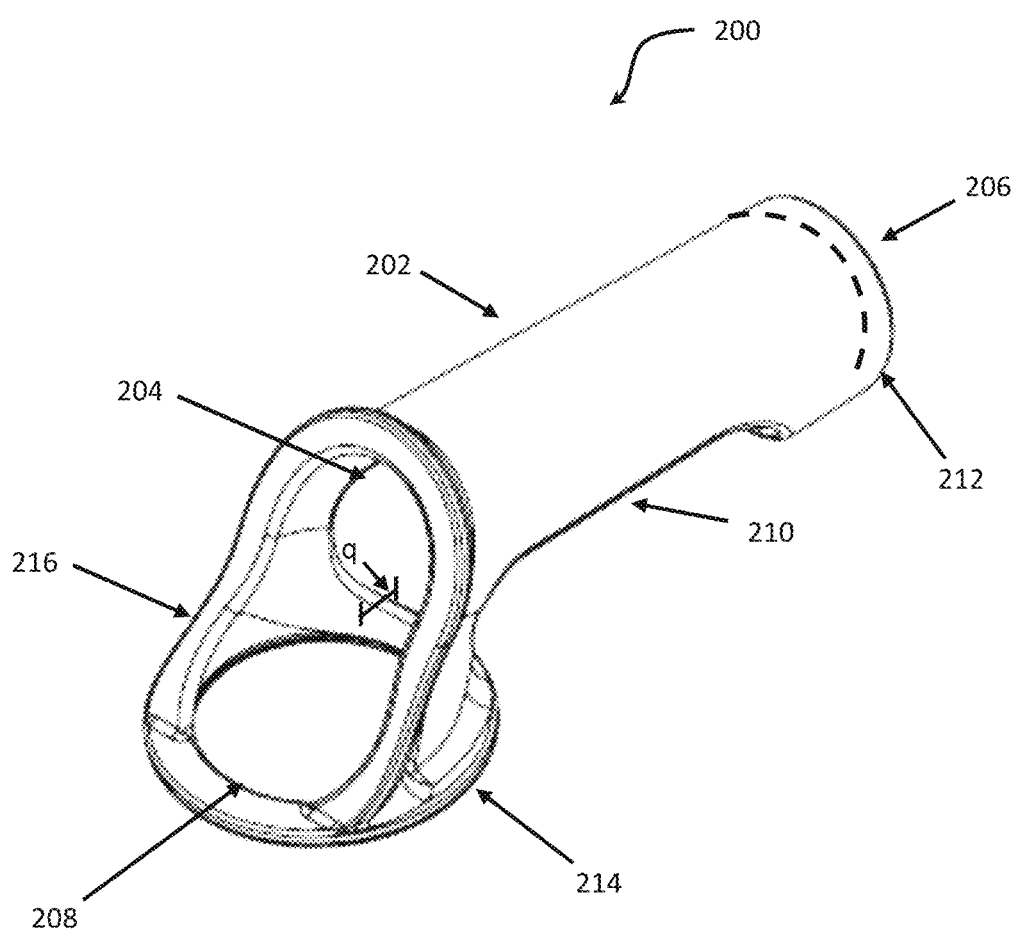
FIG. 3 is a perspective view of the elongated sleeve in accordance with an exemplary embodiment of the present invention.

FIG. 3 depicts a perspective view of elongated sleeve 200, in accordance with the present invention. As previously described, elongated sleeve 200 includes an elongated sleeve body 202 having a a first open end 206, out of which penis head 106 protrudes when elongated sleeve 200 is worn during use. Elongated sleeve body 202 includes a second open end 204 that is positioned in proximity to the penis root 104 when the apparatus is worn. Elongated sleeve body 202 further includes third opening 208 adjacent to second open end 204, and adjacent to aperture 210.

In one exemplary embodiment, first open end 206 has a circumference that is smaller than the circumference of penis 100 at penis neck 114 when penis 100 is erect and elongated sleeve 200 is being worn. Further, it is well known that during intercourse, penis scrotum 108 may become engorged with blood, making penis scrotum 108 slightly larger than when a male is not sexually aroused. Consequently, in another exemplary embodiment, the circumference of third open end 208 may be smaller than circumference of penis scrotum 108 during intercourse.

Second open end 204 may further include side wall 214 around its perimeter. Side wall 216 may be substantially perpendicular to the axis of second open end 204. Side wall 216 is preferably configured to contour to human body 112.

Third open end 208 may also include a side wall 214. In one exemplary embodiment, side wall 214 is contoured to the shape of a top portion of penis scrotum 108. Side wall 214 may be preferably substantially perpendicular to the axis of third open end 208. In another exemplary embodiment, side wall 214 and side wall 216 are configured such that they form an acute angle measured from the location on elongated sleeve 200 where side walls 214, 216 are most adjacent one to the other. Side wall 216 and side wall 214 may be comprised of the same material as is used to construct elongated sleeve body 202.

In another exemplary embodiment, first open end 206 may include a first end retaining ring 212. First end retaining ring 212 may be substantially fixed in circumference, and may be included within the thickness of elongated body 202 (described more fully below.) Similarly, third open end 208 may include a third end retaining ring 214 that may be substantially fixed in circumference, and may be included within the thickness of elongated body 202. In such instance where first end retaining ring 212, or third end retaining ring 214 are included in elongated sleeve 202, first end retaining ring 212 or retaining ring 214 apply gently pressure to penis 100 due to penis 100 expanding to full erection. The gentle pressure enhances the sexual experience of the user.

It should be noted that elongated sleeve 200 may be comprised of a pliable material. The material may be, nylon, silicon, polydimethylsiloxane, polypropylene, plastic or other material simulating real skin, such as is used in prosthetics, of a thickness, q, as shown in FIG. 3. The thickness of elongated sleeve 200 is such that it does not provide an abnormal amount of girth to penis 100 when elongated sleeve 200 is worn. For example, elongated sleeve thickness may not be more than 05. inches.

Figure 4:
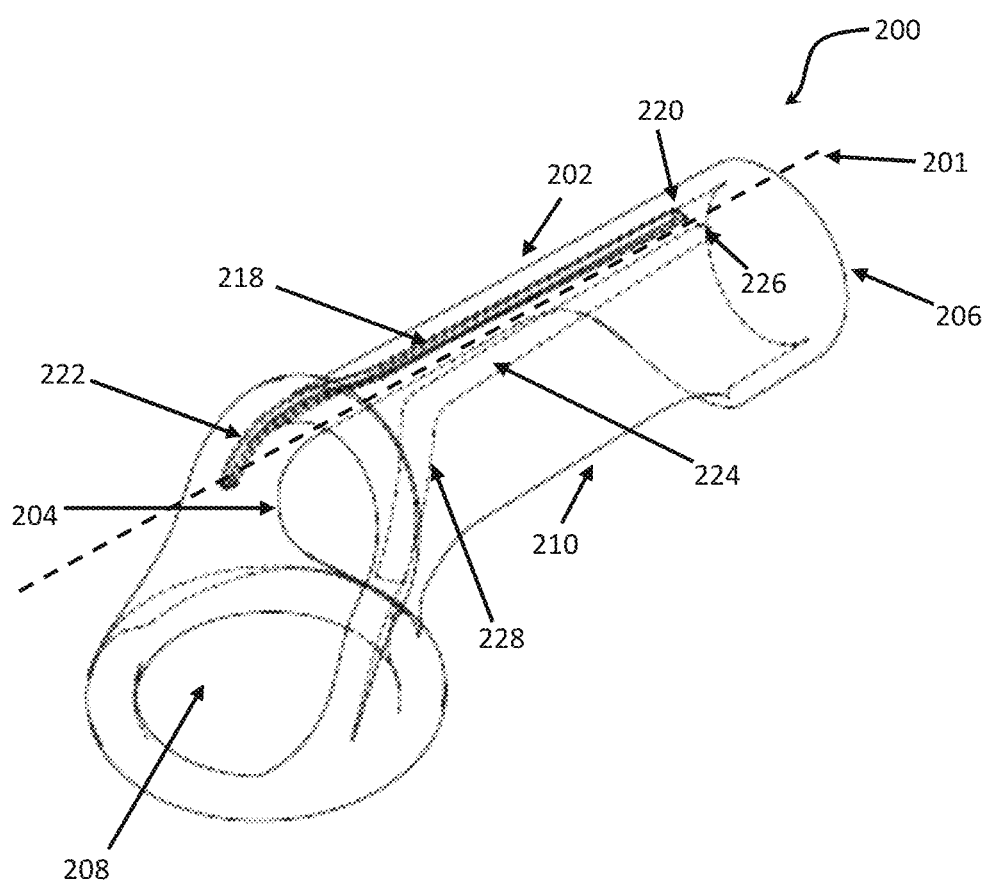
FIG. 4 is a transparent view of the elongated sleeve showing exemplary penile support bars in accordance with an exemplary embodiment of the present invention.

Elongated sleeve 200 may further include one or more support braces positioned within elongated sleeve 200 for propping up penis 100 when penis 100 is flaccid or semi-erect. FIG. 4 depicts a transparent view of an exemplary embodiment of elongated sleeve 200 in accordance with the present invention. FIG. 4 further shows a midline 201 which substantially defines the location on elongated sleeve body 202 that is on an upper portion of elongated sleeve body 202. In one exemplary embodiment, midline 201 is in substantial proximity to the topmost portion of sleeve body 202. As used herein, midline 201 is parallel to the longest portion of elongated sleeve 200. In still another exemplary embodiment, midline 201 is positioned on elongated sleeve body 202 at a position opposite aperture 210. It should be noted, that midline 201 is described here to aid in the further description of elongated sleeve 200. As such, elongated sleeve body 202 may be comprised of a single unit where the midline is not readily visible, or it may be comprised of a molded material where the midline is visible.

With further reference to FIG. 4, elongated sleeve body 202 may include at least one penis support brace 218. Penis support brace 218 may be located within elongated sleeve body 202. Penis support brace 218 may be positioned within the material forming thickness, q. Penis support brace 218 may be substantially elongated. The length of penis support brace 218 may be such that it is substantially equal to the length of elongated sleeve body 202. In some embodiments, the length of penis support brace 218 may be more than half the length of elongated sleeve body 202. Penis support brace 218 may include a penis support brace first end 220. Penis support brace first end 220 may be located substantially in proximity to first open end 206. Penis support brace 218 may include a penis support brace second end 222. A penis support brace second end 222 may be positioned in proximity to second open end 204. In one exemplary embodiment, penis support brace second end 222 may be contoured. That is, penis support brace second end 222 may be angular in shape. More particularly, penis support brace second end 222 may be angled or curved such that penis support brace second end 222 substantially mimics the curvature of penis 100 at penis root 104. That is, penis support brace second end 222 may curve toward third open end 208.

Penis support brace 218 may be located to a first side of midline 201. In another embodiment, penis body 202 may include at least a second penis support brace 224, of similar construction as was described with respect to penis support brace 218. Second penis support brace 224 may be located within penis body 202, in similar manner as was described with respect to penis support brace 218. Second penis support brace 224 may also be located on a second side of midline 201, where the first side of midline 201 is on an opposite side of midline 201 than is the second side of midline 201. Further still, penis support brace 224 may be substantially elongated. The length of penis support brace 224 may be substantially equal to the length of elongated sleeve body 202. Second penis support brace 224 may include a first end 226 that may be substantially positioned in proximity to first open end 206. A second penis support brace second end 224 may be positioned in proximity to second open end 204. In one exemplary embodiment, second penis support brace second end 228 may be contoured. That is, second penis support brace second end 228 may be angular in shape. More particularly, second penis support brace second end 228 may be angled or curved such that penis support brace second end 228 has a curvature substantially similar to the curvature of penis 100 at penis root 104. That is, penis support brace second end 228 may curve toward third open end 208.

Figure 5:
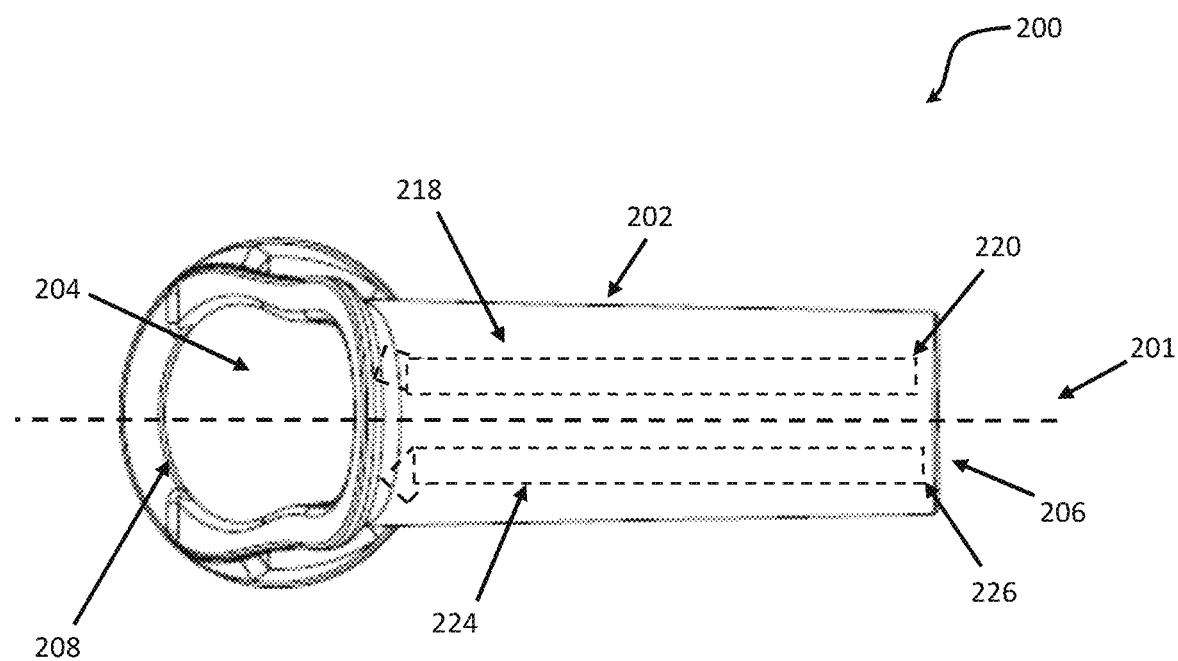
FIG. 5 is an overhead view of the elongated sleeve showing exemplary penile support bars in accordance with an exemplary embodiment of the present invention.

FIG. 5 shows an overhead view of an elongated sleeve according to an exemplary embodiment of the present invention. As shown, midline 201 is shown in the middle of elongated sleeve 200. In the embodiment shown, midline 201 shows where elongated sleeve 200 may be defined to have an equal amount of material on either side of midline 201. In such instance, penis support brace 218 may be positioned substantially on a first side of midline 201. Penis support brace 224 may be positioned substantially on a second side of midline 201, where the first side of midline 201 is in a first half of elongated sleeve body 202 and the second side of midline 201 is in a second half of elongated sleeve body 202. In one exemplary embodiment, the first side of midline 201 and the second side of midline 201 are mutually exclusive.

As previously noted, during use, a male inserts penis 100 into elongated sleeve 200. For example, penis head 106 is inserted through second open end 204 and through first open end 206 such that first open end 206 rests in proximity to in proximity to penis neck 114. The penis scrotum 108 may be inserted through third open end 208.

A male would use the present invention during intercourse. A male may use elongated sleeve 200 in the event that penis 100 does not get fully erect, or if penis 100 is semi-erect. Penis support brace 216 and penis support brace 218 may be used to prop up the semi-erect penis so that the penis may simulate erectness.

Figure 6:
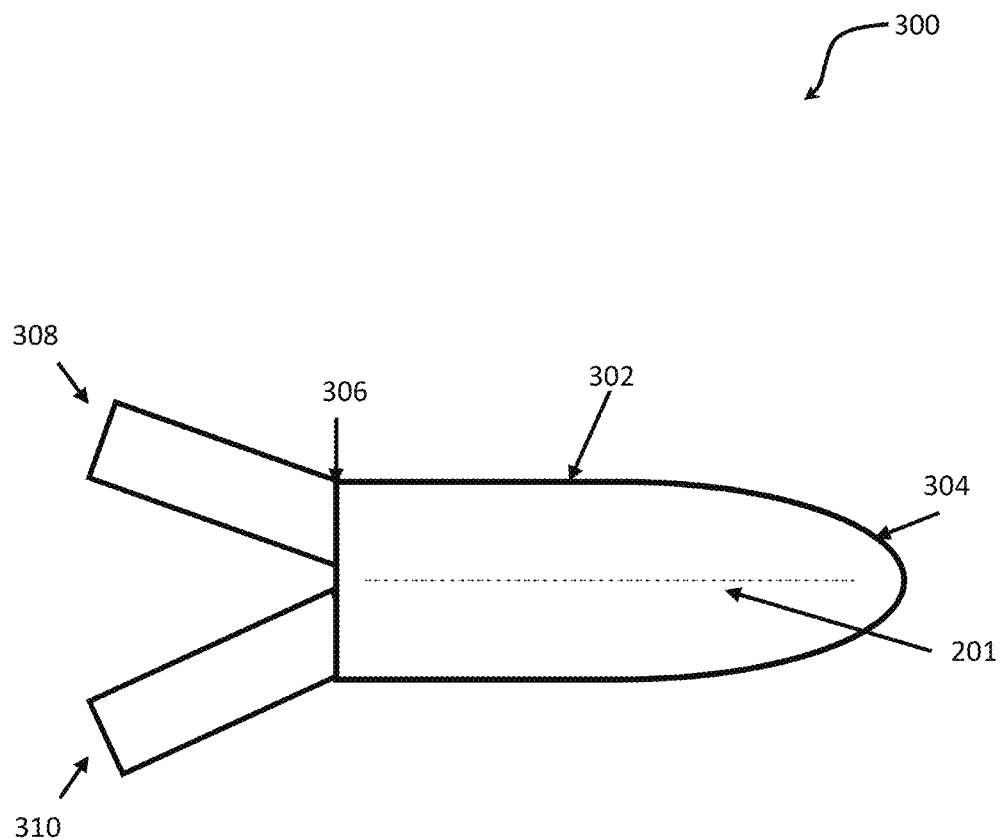
FIG. 6 is an illustration of an exemplary penile support according to an exemplary embodiment of the invention.

FIG. 6 depicts an alternate embodiment of a penile support brace 300 that may be used with elongated sleeve 200 in accordance with exemplary embodiments of the present invention. Penile support brace 300 may include an elongated penile support brace body 302 having a penile support brace first end 304 and a penile support brace second end 306. The length of penis support brace body 302 may be such that it is substantially equal to the length of elongated sleeve body 202. In some embodiments, the length of penis support brace body 302 may be more than half the length of elongated sleeve body 202.

Figure 7:
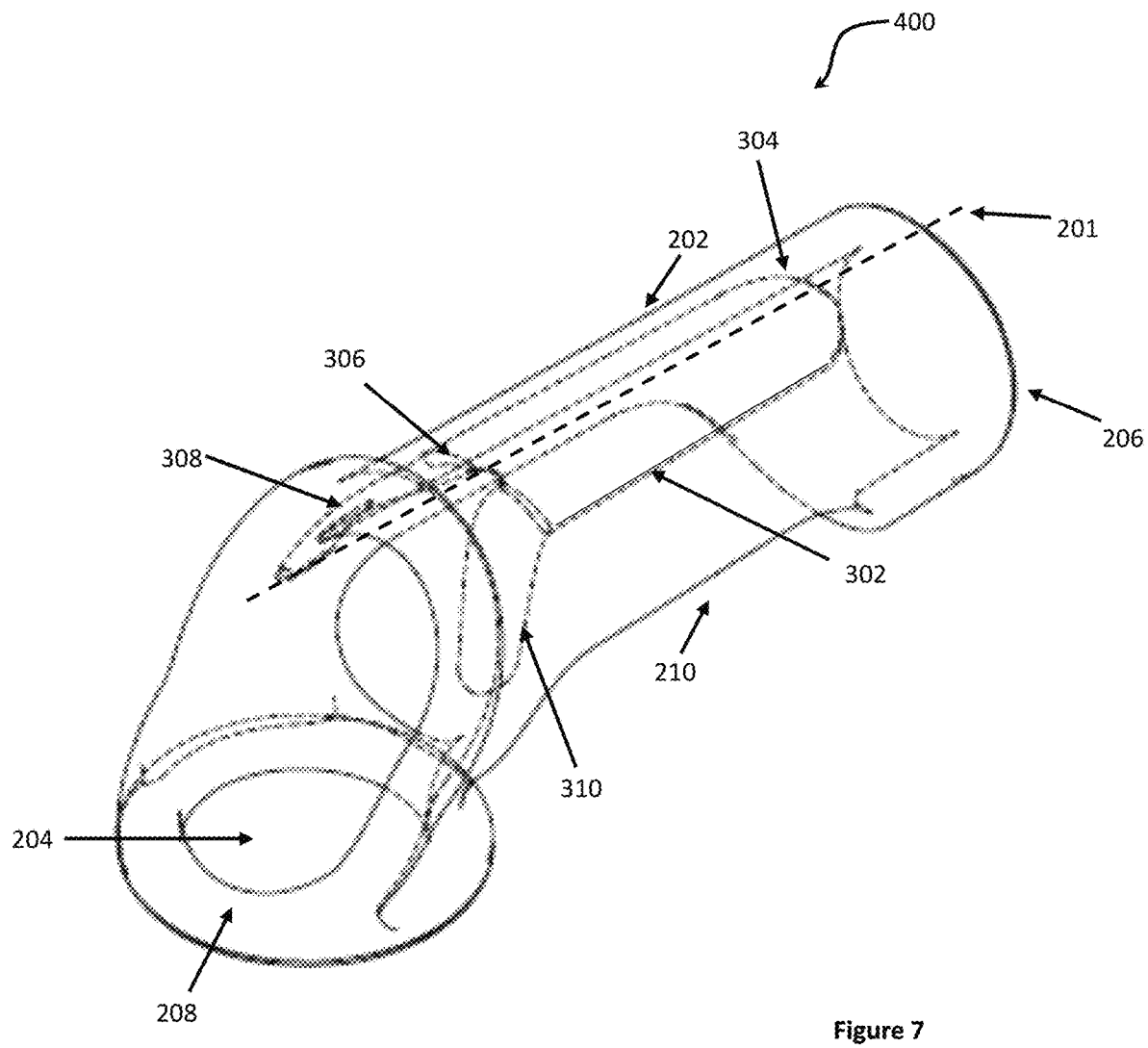
FIG. 7 is a transparent view of the elongated sleeve showing an alternate embodiment of a penile support in accordance with present invention.

As shown in FIG. 7, penile support brace first end 304 may be located substantially in proximity to first open end 206. Penile support brace second end 306 may be positioned in proximity to second open end 204.

In one exemplary embodiment, penis support brace second end 306 may include a penile support brace first projection 308 in abutment with penile support brace second end 306. Penile support brace second end 306 may further include a penile support brace second projection 310 in abutment with penile support brace second end 306. In some embodiments, penis support brace 300 comprises a unitary piece. The unitary piece may be comprised of the same material composition throughout.

Penile support brace first projection 308 may be angular in shape. More particularly, penis support brace first projection 308 may be angled or curved such that penis support brace first projection 308 substantially mimics the curvature of penis 100 at penis root 104. That is, penis support brace first projection may curve toward third open end 208.

Similarly, penile support brace second projection 310 may be angular in shape. More particularly, penis support brace second projection 310 may be angled or curved such that penis support brace second projection 310 substantially mimics the curvature of penis 100 at penis root 104. That is, penis support brace first projection 308 may curve toward third open end 208. Penile support brace first projection 308 and penile support brace second projection 310 may not curve to the same side of penis 100 at penis root 104. As used herein, sides of penis 100 is described with respect to midline 201.

Penile support brace 300 may have similar material composition and similar general placement inside elongated sleeve body 202. That is, penis support brace 300 may be located within elongated sleeve body 202. More particularly, penile support brace 300 may be located along midline 201, such that at least penile support brace first projection 308 and penile support brace second projection 310 are positioned substantially proximate midline 201. In one exemplar embodiment, penile support brace first projection 308, and penile support brace second projection 310 are each positioned on opposite sides of midline 201. Further, penile support brace 300 may be positioned within the material forming thickness, q.

It should be noted that various embodiments of the invention are described with respect to the individual elements of the invention. However, the invention may be formed of a single unit. Further still, such modifications are within the spirit and scope of the invention.

The invention claimed is:

1. An apparatus for supporting a human penis, wherein the human penis includes a penis scrotum for containing human testicles, a penis root in communication with the penis scrotum, a penis shaft in communication with the penis root, and a penis neck in communication with the penis shaft, and a penis head in communication with the penis neck, wherein the penis shaft has a top half and a bottom half, the apparatus comprising:
  b. an elongated sleeve for enclosing the penis shaft, the elongated sleeve having,
    i. a first open end, wherein the first open end is positioned to be in proximity to the penis neck when the elongated sleeve is worn,
    ii. a second open end, wherein the second open end is positioned along a portion of the bottom half of a length of the elongated sleeve, and wherein the second open end is positioned opposite the first open end, and wherein the second open end is positioned in proximity to the root of the penis when the elongated sleeve is worn,
    iii. a third open end, the third open end being positioned adjacent to the second open end, wherein the third open end is positioned to receive the penis scrotum when the elongated sleeve is worn,
    iv. a first elongated penile support brace positioned along a first lateral side of the elongated sleeve, the first elongated penile support brace having a first end in proximity to the penis root, the first elongated penile support brace having a second end in proximity to the penis head,
    v. a first penile support brace in abutment with the first end of the first elongated penile support bar, wherein the first penile support brace is angular in shape, wherein the first penile support brace angles toward a portion of the bottom half of the penis shaft.

2. An apparatus according to claim 1, further including a second elongated penile support brace positioned along a second lateral side of the elongated sleeve, the second elongated penile support bar having a first end in proximity to the penis root, the second elongated penile support brace having a second end in proximity to the penis head, and
a second penile support brace in abutment with the first end of the second elongated penile support brace, wherein the second penile support brace is angular in shape.

3. An apparatus according to claim 1, wherein the first penile support brace angles toward the third open end.

4. An apparatus according to claim 3, wherein the elongated penile support brace is comprised of ABS plastic.

5. An apparatus according to claim 4, wherein the elongated sleeve has a thickness, q, comprised of nylon, and wherein the elongated penile support bar is included within the elongated sleeve thickness, q.

6. An apparatus according to claim 4, wherein the elongated sleeve has a thickness, q, comprised of nylon, and wherein the first elongated penile support bar and the second elongated penile support bar are included within the elongated sleeve thickness, q.

7. An apparatus according to claim 1, wherein the first elongated penile support brace and the first penile support brace form one contiguous brace.

8. An apparatus according to claim 1, wherein the elongated penile support bar is comprised of ABS plastic.

9. An apparatus for supporting a human penis, wherein the human penis includes a penis scrotum for containing human testicles, a penis root in communication with the penis scrotum, a penis shaft in communication with the penis root, and a penis neck in communication with the penis shaft, and a penis head in communication with the penis neck, the apparatus comprising:
  a. an elongated sleeve for enclosing the shaft of the penis, the elongated sleeve having
    i. a first open end, wherein the first open end is positioned to be in proximity to the penis head when the elongated sleeve is worn,
    ii. a second open end, wherein the second open end is positioned along a length of the elongated sleeve, and wherein the second open end is positioned opposite the first open end, and wherein the second open end is positioned to receive the penis root when the elongated sleeve is worn,
iii. a third open end, the third open end being positioned adjacent to the second open end, wherein the third open end is positioned to receive the penis scrotum when the elongated sleeve is worn, and
wherein the elongated sleeve includes an aperture in proximity to the second open end, wherein the elongated sleeve aperture in proximity to the third open end, and wherein the elongated sleeve aperture is positioned to expose a portion of the penis shaft when the elongated sleeve is worn,
iv. a first elongated penile support bar positioned along a first lateral side of the elongated sleeve, the first elongated penile support bar having a first end in proximity to the penis root, the first elongated penile support bar having a second end in proximity to the penis head, and
v. a first penile support brace in abutment with the first end of the first elongated penile support brace, wherein the first penile support brace is angular in shape.

10. An apparatus according to claim 9, further including a second elongated penile support brace positioned along a second lateral side of the elongated sleeve, the second elongated penile support brace having a first end in proximity to the penis root, the second elongated penile support brace having a second end in proximity to the penis head, and
a second penile support brace in abutment with the first end of the second elongated penile support brace, wherein the second penile support brace is angular in shape.

11. An apparatus according to claim 9, wherein the elongated sleeve is comprised of nylon.

12. An apparatus according to claim 9, wherein the first lateral side of the elongated sleeve is positioned on an opposite lateral side to the second lateral side of the elongated sleeve.

13. An apparatus for supporting a human penis, wherein the human penis includes a penis scrotum for containing human testicles, a penis root in communication with the penis scrotum, a penis shaft in communication with the penis root, and a penis neck in communication with the penis shaft, and a penis head in communication with the penis neck, wherein the penis shaft includes a top half and a bottom half, the apparatus comprising
a. an elongated sleeve for enclosing the shaft of the penis, the elongated sleeve including a length and a midline along the length, the elongated sleeve further having,
i. a first open end, wherein the first open end is in proximity to the glans of the penis when the elongated sleeve is worn,
ii. a second open end, wherein the second open end is configured to be positioned along the length of the elongated sleeve, and wherein the second open end is positioned opposite the first open end, and wherein the second open end is positioned to receive the root of the penis when the elongated sleeve is worn,
iii. a third open end, the third open end is configured to be positioned adjacent to the second open end, wherein the third open end is positioned to receive the penis scrotum when the elongated sleeve is worn, and
iv. an elongated penile support brace positioned along an elongated sleeve midline, the elongated penile support brace having a first end in proximity to the penis root, the first elongated penile support brace having a second end in proximity to the penis head, and
v. a first penile support brace in abutment with the first end of the first elongated penile support brace, wherein the first penile support brace is angular in shape.

14. An apparatus according to claim 13, further including a second penile support brace in abutment with the first end of the elongated penile support brace, wherein the second penile support brace is angular in shape.

15. An apparatus according to claim 14, wherein the first penile support brace angles is positioned on a first side of the third open end.

16. An apparatus according to claim 13, wherein the first penile support brace angle is positioned on a first side of the third open end.

* * * * *